(12) United States Patent
Ulert et al.

(10) Patent No.: US 6,570,503 B1
(45) Date of Patent: May 27, 2003

(54) EMERGENCY SIGNALING DEVICE

(76) Inventors: Izaak A. Ulert, 2929 Post Oak Blvd., Apt. 402, Houston, TX (US) 77056; Henry Lang, 43 Winter Wheat Pl., The Woodlands, TX (US) 77381

( * ) Notice: Subject to any disclaimer, the term of this patent is extended or adjusted under 35 U.S.C. 154(b) by 0 days.

(21) Appl. No.: 09/556,751

(22) Filed: Apr. 21, 2000

(51) Int. Cl.[7] ................................................ G08B 23/00
(52) U.S. Cl. ............................... 340/573.1; 340/573.6; 340/573.7
(58) Field of Search ............................. 340/539, 573.1, 340/573.3, 573.4, 573.7, 825.36, 825.49; 128/903, 904; 600/300

(56) References Cited

U.S. PATENT DOCUMENTS 4,829,285 A * 5/1989 Brand et al. ............. 340/573.4
5,652,570 A * 7/1997 Lepkofker ............... 340/573.4
6,028,514 A * 2/2000 Lemelson et al. ....... 340/573.1
6,160,478 A * 12/2000 Jacobsen et al. ........ 340/573.1

* cited by examiner

Primary Examiner—Vah T. Trieu
(74) Attorney, Agent, or Firm—Valerie K. Friedrich

(57) ABSTRACT

An emergency signal device for use by those with medical conditions having means to detect the occurrence of a change in attitude in conjunction with a shock and an alarm means including audible messages alerting bystanders to the wearer's medical problems. The emergency signal device may also include means to activate the alarm means in the event the wearer exits a pre-specified geographic area, or at pre-specified time intervals. The emergency signal device may also include cellular and global positioning satellite means to automatically determine and transmit the location of the emergency signal device to a cellular base station upon activation of the alarm. The emergency signal device may further include means for activating existing emergency telephone notification systems.

6 Claims, 3 Drawing Sheets

EMERGENCY SIGNALING DEVICE

FIELD OF THE PRESENT INVENTION

This invention relates to an Emergency Signaling Device (ESD) which is worn by individuals at risk of falling, becoming unconscious or of becoming lost and which alerts bystanders that the individual wearing the ESD is in some such distress. More particularly, the ESD of the present invention is comprised of means for sensing that the wearer has sustained a shock and fallen, or has become lost, and an alarm and/or other means of communicating or relating messages for alerting bystanders. The device of the present invention does not require any action on the part of one wearing the device to activate the alerting function.

BACKGROUND OF THE INVENTION

Numerous situations exist in which it would be advantageous to draw the attention of bystanders to an individual in need of medical assistance. For instance, there are many medical conditions, such as epilepsy, diabetes, narcolepsy, and cardiac and circulatory deficiencies, which put an individual at risk of a convulsive or non-convulsive seizure or which may cause an individual to loose his or her consciousness or balance. Yet other medical conditions, such as Alzheimer's, may cause an individual to wander off and become lost.

When such events occur, bystanders often do not pay attention to such a fallen, dazed, unsteady or lost individual, thinking that it is a case of inebriation or drug abuse. Frequently, the individual having this problem is unable to communicate his distress or the cause of his problem or to effectively solicit the assistance of bystanders.

Personal alarm devices which are currently available have deficiencies which are met by the device of the present invention. For example, the personal alarm disclosed in U.S. Pat. No. 5,475,368 is used primarily for defensive purposes but must be activated by the person in distress. Therefore, an individual who has lost consciousness, motor control or who do not realize they are in distress (such as a wandering Alzheimer's patient) cannot or do not activate the alarm of the device claimed in the '368 patent.

U.S. Pat. No. 3,866,204 discloses an electronic medical warning device which activates an alarm, following a delay period, upon the closing of an attitude switch. The device of '204 patent, however, could undesirably activate. For example, should the wearer of the '204 device lie down for a period greater than the delay period, the alarm would activate.

Therefore, it would be advantageous to have a device which would sound some sort of audible alarm or signal when the wearer sustains a shock in conjunction with a change in attitude. It would be advantageous for such audible alarm or signal to include a voice message alerting bystanders to the wearer's condition or medical problem. It would be further advantageous to have a device which may be automatically activated at pre-set time intervals or upon the exit of the device from a specified location. It would be further advantageous to have such a device which could also be manually activated by an individual in distress, if such individual were physically and mentally capable of activating the device.

SUMMARY OF THE PRESENT INVENTION

The present invention addresses the deficiency of prior art personal alarm devices by providing a device which automatically activates the alarm function upon the occurrence of certain events, such as a change in attitude in conjunction with sustaining a shock, upon the exit of the device from a specified area or upon activation by either the wearer or a third party.

In a particular embodiment of the present invention, the ESD contains a means for detecting attitude and shock and which more specifically detects whether the individual wearing the ESD is in an upright or prone position. In the event the individual wearing the alarm looses consciousness or otherwise falls, the device would activate an audible alarm which would draw the attention of bystanders to the individual in distress.

In the event the individual falls to the ground and sustains a shock, greater than that normally imposed by walking, the device would activate an audible alarm which would alert bystanders but may also play a voice message indicating the wearer's medical conditions.

In another embodiment of the present invention, the ESD contains an alarm which is activated if the ESD is transported beyond a pre-set distance from a base station. Such an embodiment would be most useful with cognitively impaired, such as Alzheimer's patients, who may wander and become lost. Such a device would sound an audible alarm and/or voice message requesting assistance and identifying the caretakers of the patient upon activation. In another embodiment of particular use, the ESD may contain an alarm which is time-dependent and which is set to sound at certain pre-set intervals or times.

DETAILED DESCRIPTION OF THE INVENTION

The Emergency Signal Device ("ESD") of the present invention is comprised in a portable casing similar in size and shape to a typical beeper or cellular telephone. The ESD may contain a clip or other means for fastening onto the clothing of the user or may be placed in a holder which is then fastened to the clothing of the user. In the alternative, the ESD may be hung around the neck in necklace fashion using any acceptable lacing material.

Figure 1:
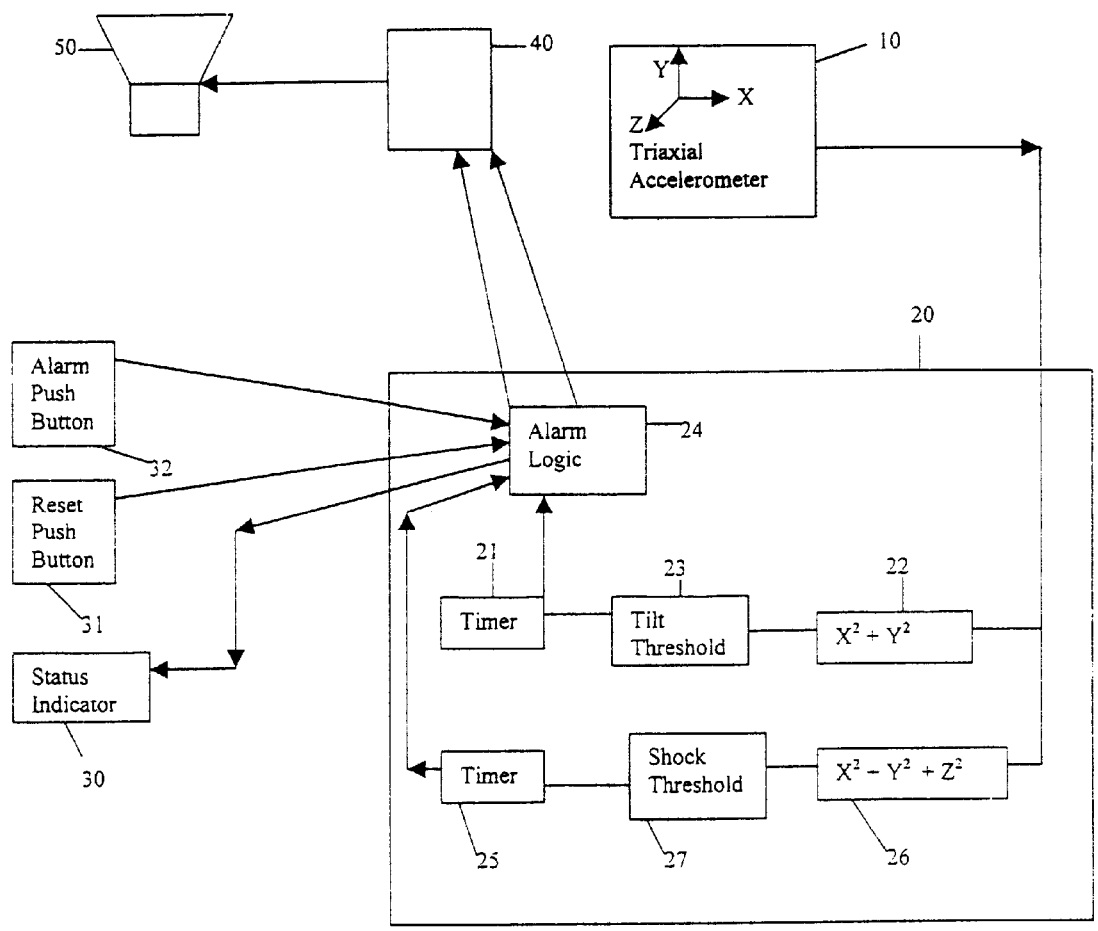
FIG. 1 is a high level diagram of a first preferred embodiment of the Emergency Signal Device.
Figure 2:
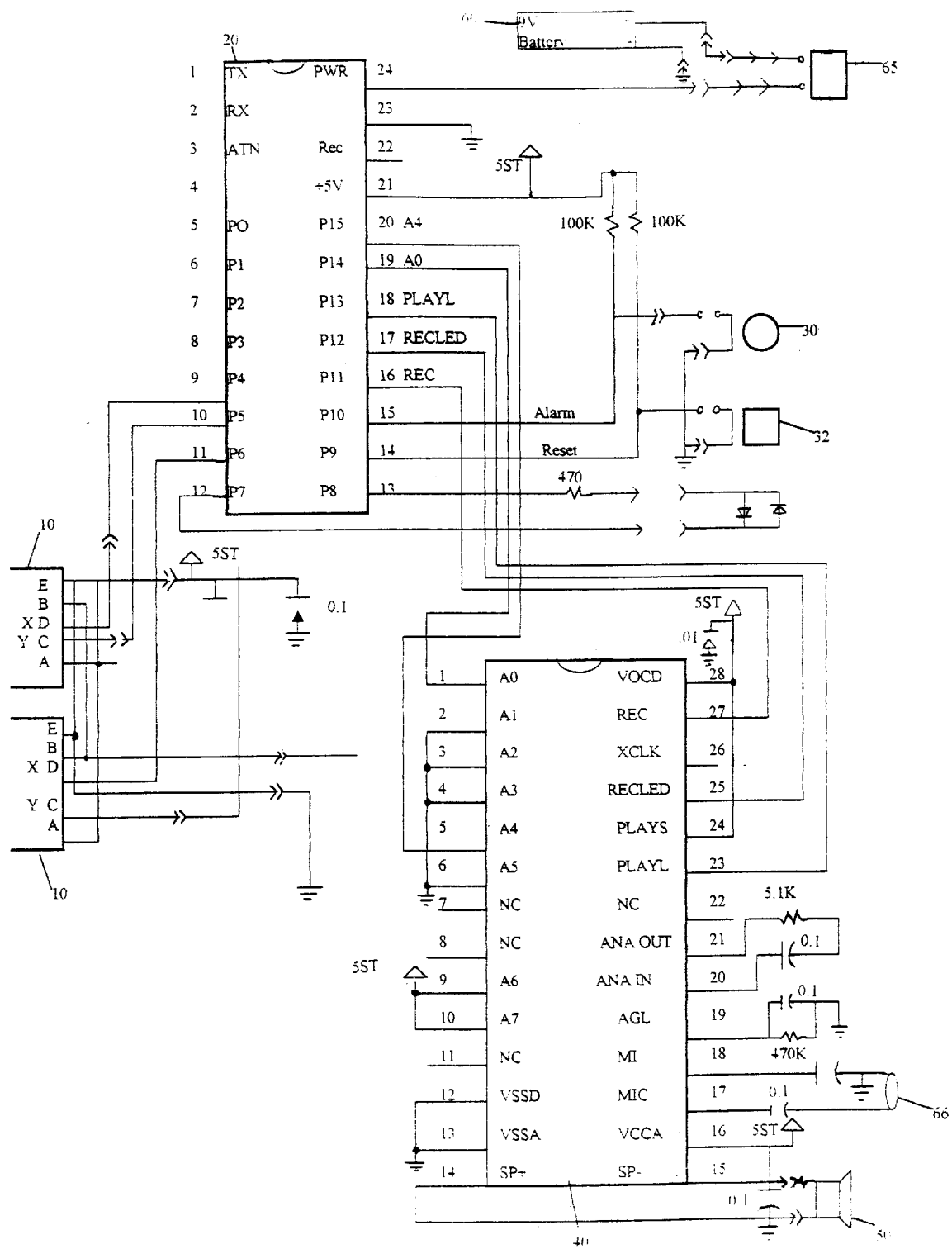
FIG. 2 is a wiring diagram of a first preferred embodiment of the Emergency Signal Device.

Referring first to FIG. 1, the functions of a first preferred embodiment of the ESD of the present invention may be illustrated. In the first preferred embodiment, the ESD contains means for detecting attitude and shock. To detect attitude in three dimensions, the ESD may contain a single triaxial accelerometer, two biaxial accelerometer or three uniaxial accelerometer. In FIG. 1, the ESD is illustrated as possessing a single triaxial accelerometer 10. It win be understood that in the event two biaxial accelerometers are utilized, one axis of one of the accelerometers would be left idle. In the preferred embodiment, atriaxial accelerometer, available from Analog Devices, Inc., part number ADXL05EM-3, is used. It will be understood, however, that any of a number of commercially available tri-, bi- or uni-axial accelerometers, such as biaxial accelerometer ADXL202EB from Analog Devices, Inc., may be used. A microprocessor 20 is pre-programmed to accept input from accelerometer 10, to analyze such input and to sound an alarm in the event the attitude of the ESD unit is outside pre-programmed thresholds for a time period beyond a pre-programmed time limit in conjunction with the detection of a shock above a pre-set threshold within a pre-set time period of the change in attitude. Although a number of commercially available microprocessor may be used, in the preferred embodiment, microprocessor 20 is obtained from Parallax, Inc., part number Basic Stamp II Module. As shown in FIG. 1, the microprocessor program contains a timing routine 21 for attitude which is calculated using an attitude algorithm 22 using input from accelerometer 10. Microprocessor 20 further contains a timing routine 25 for determining the time difference between a change in attitude and the occurrence of a shock. Microprocessor 20 further contains a shock algorithm 26 which uses data from accelerometer 10 to calculate a shock and to determine whether the shock is greater or less than a pre-set threshold value. Microprocessor 20 further includes an alarm logic 24 which determines the nature, sequence and length of the alarm or messages sounded. Alarm logic 24 may further control a status indicator 30 which is visible on the exterior of the ESD. It will be understood that the status indicator 30 may be any of a variety of currently available lighting means, such as light emitting diodes. In, the preferred embodiment, status indicator 30 displays as green to indicate that the alarm has not been activated and displays as red to indicate that the alarm has been activated. Alarm logic 24 further permits the alarm to be discontinued through use of a reset button 31 or to be manually activated by use of a manual button 32. When activated, alarm logic 24 will activate the multiple message storage device 40 to play one or more pre-recorded alarm sounds or voice messages through external speaker 50. Multiple message storage device 40 may be any of a variety of commercially available storage devices. In the preferred embodiment multiple message storage device 40 is the Multiple Voice Message from Information Storage Devices, Inc., part number ISD 1416P. External speaker 50 may be any of a number of commercially available speakers which is compatible with remaining components of the ESD and which meets the size requirements of the ESD. Referring now to FIG. 2, a detailed wiring diagram of a first preferred embodiment of the ESD is shown. In addition to the components discussed in connection with FIG. 1, the ESD is comprised of a battery 60 and an on/off switch 65. A microphone jack 66 is connected as shown to the multiple message storage device 40 so as to make customized pre-recorded messages.

Figure 3:
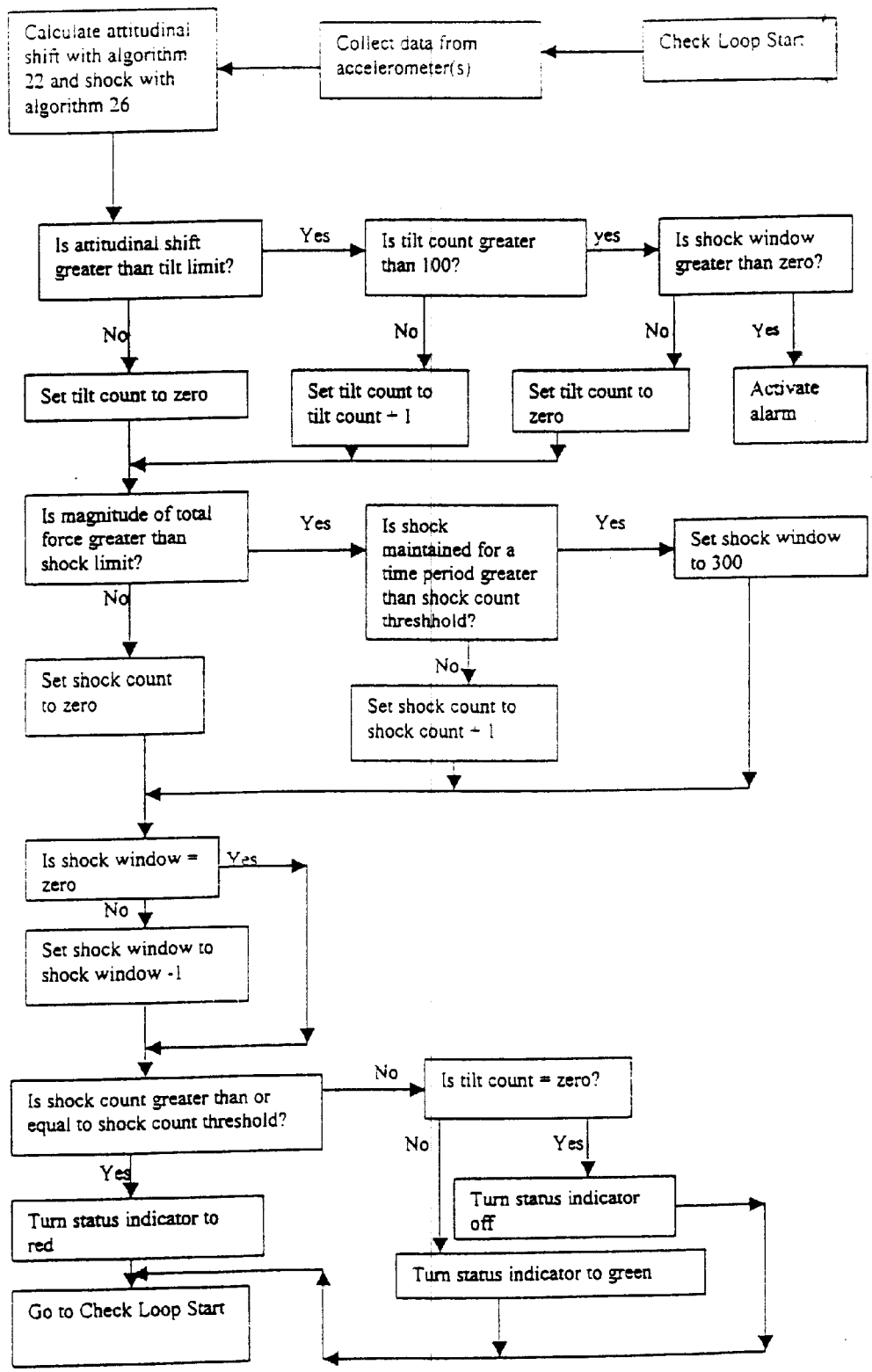
FIG. 3 is a flow diagram of the primary mode of operation of a first preferred embodiment of the Emergency Signal Device.

FIG. 3 displays the operational mode, also called the check loop, of the ESD. The operational mode includes a loop in which data is collected from accelerometer 10 and then processed by algorithms 22 and 26. If the attitudinal shift, as calculated by algorithm 22 is greater than the pre-programmed attitudinal shift limit, and if that attitudinal shift is maintained for a time period, called the tilt count, greater than a pre-programmed limit, called the tilt count threshold, the amount of shock sustained is checked. If a shock greater than a pre-programmed shock limit is detected within a time period of about three times the length of the tilt count threshold, the alarm is activated. The time period before and after an attitudinal shift during which a shock must occur to activate the alarm is called the shock window. If a shock greater than the shock limit is sustained outside the shock window, the audible alarm is not activated but the status indicator 30 is set to red and the operational loop is repeated.

It will be understood that the ESD may be placed in other modes. For example, in an initialization mode, variables such as the tilt count and shock count are set to zero. In the initialization mode, the mode which the user of the ESD wishes to access may also be set. In another mode, called mode zero, single voice messages may be recorded and checked. In yet another mode, mode one, multiple voice messages may be recorded and checked. A final mode of operation is called the alarm mode and is the process which occurs upon activation of the alarm. One method of programming a prototype of the ESD is shown in Appendix A. It will be understood that the tilt limit, tilt count threshold, shock limit and shock count threshold may be pre-programmed to some u reasonable limits or in the alternative, may be set by individual users, depending upon each users level of activity and flexibility. For example, for a wheelchair bound patient, the tilt limit may be set to detect even slight attitudinal changes and the tilt count threshold set low so as to be the equivalent of a few seconds, as the patient would not be expected to bend over. However, if the user is a fairly active person with some recurrent disability, such as epilepsy, the tilt limit may be set so as to correspond to a completely prone position. Similarly, the shock limit and shock count threshold may correspond to the user's level of activity. For example, an ESD used by an ambulatory patient should be set such that the shock sustained from normal walking lies lower than the shock limit so that walking does not activate the alarm.

In a second preferred embodiment of the ESD, an additional timing routine, a periodic timing routine, may be included so as to cause the automatic activation of the alarm at certain pre-set time intervals. In such embodiment, the alarm would be deactivated through reset button 31. It will be understood that in such an embodiment, microprocessor 20 would contain additional programming, a periodic timing routine, to execute such additional functions.

In a third preferred embodiment of the ESD, a proximity detector may be included so as to activate the alarm if the ESD is transported outside a pre-set geographic area. Such proximity detectors, such as those used to track parolees, are commercially available. It will be understood that microprocessor 20 may be programmed to accept input from such a proximity detector and to activate the alarm upon movement of the ESD outside such pre-set geographic area. It will be further understood that microprocessor 20 may be programmed as to sound he alarm only if the ESD is moved outside the pre-set geographic limits for a time period outside certain acceptable limits.

In a fourth preferred embodiment of the ESD, the ESD contains a global positioning unit ("GPU"). Global positioning technology utilizing orbiting satellites is now commercially available. It will be understood that microprocessor 20 may be programmed to activate the GPU upon activation of the alarm. In order to minimize the size of the ESD, the device of the fourth preferred embodiment would incorporate cellular digital packet data transmission ("CDPD") technology which permits the transmission of data through cellular frequencies. In such ESD, activation of the alarm would cause a cellular transmitter to dial out to a pre-programmed emergency number which rings at a cellular base station. Upon receipt of an incoming call from the ESD, the cellular base station, in constant communication with a global positioning satellite ("GPS"), transmits the coordinates of the GPS satellite to the ESD. The ESD then receives, through CDPD, data from the satellite and transmits such data to the cellular base station. Computers located at the cellular base station calculate the location of the ESD and send a distress call, along with the ESD location, to the appropriate authorities, such as police. Because the calculation of the location of the ESD is done by computers located at the cellular base station, the size of the ESD may be minimized. ESDs of this fourth preferred embodiment would, therefore, be further comprised of a cellular antenna, cellular receiver and transmitter, and global positioning satellite antenna, receiver and transmitter.

In a fifth preferred embodiment, the ESD is further comprised of a means for alerting or activating existing prior art telephone emergency notification systems. For example, Radio Shack product number 49-2559 utilizes a pendant style remote control device which, when activated by manually depressing a button on the remote control, activates a phone dialer console. The phone dialer console may be pre-programmed with up to four telephone numbers to dial upon activation. In the fifth preferred embodiment, the ESD further comprises a means for activating such existing systems upon activation of the alarm.

APPENDIX A

```
'model4.bs2
'\\\\\\\\\\\\\\\\\\\\\\\\\\\\\\\\\\\\\\\\\\\\\\\\\\
' mode zero allows single message to be recorded and played back
' buttons on unit. red button records, green button plays back.
' this has a core that does X^2+Y^2+Z^2 type calculations
minX1 data (1)
minXh data (1)
maxX1 data (1)
maxXh data (1)
maxY1 data (1)
minYh data (1)
maxY1 data (1)
maxYh data (1)
minZ1 data (1)
minZh data (1)
maxZ1 data (1)
maxZh data (1)
mode var nib
i var byte
LRED con 7
LGREEN con 8
PLAYL var OUT13
AO var OUT14 ' high means skip through message
A4 var OUT15 ' high means reset message counter
REC var OUT11
RECLED var IN12
ALARM var IN10
P_ALARM con 10
P_RST con 9
RST var IN9
PX con 5 ' IO bit with X axis accel
PY con 4 ' IO bit with Y axis accel
PZ con 6 ' IO bit with Z axis accel
' SETTLE_THRESHOLD con 20
' SETTLE_TIME con 50
' SETTLE_PIN var nib
' SETTLE_VAL var word
Xmid var byte
Ymid var byte
Zmid var byte
Xval var byte
Yval var byte
Zval var byte
ACC var word
WTEMP var word
WTEMP2 var word
WTEMP3 var word
XY2max var byte ' threshold for X^2+Y^2
Mag2max var byte ' threshold for X^2+Y^2+Z^2
tiltlim var byte
shocklim var byte
tilt_cnt var byte
shock_cnt var byte
```

-continued

APPENDIX A

```
BTEMP var WTEMP3.lowbyte
BTEMP2 var WTEMP3.highbyte
CNT var byte
shockwindow var word
shock_cnt_thresh var nib
XSCALE con 8
YSCALE con 8
ZSCALE con 7
start:
HIGH 15
HIGH 14
HIGH 13
HIGH 11
PLAYL = 1
A0 = 0
A4 = 0
REC = 1
INPUT 4
INPUT 5
INPUT 6
tilt_cnt=0
shock_cnt=0
mode = 15 − INA
debug "mode:", DEC mode, cr
if mode=0 then zero_mode
nap 5
for i=1 to mode
GOSUB red_on
NAP 4
GOSUB led_off
NAP 4
next
goto mode_disp_end
zero_mode:
GOSUB green_on
NAP 4
GOSUB led_off
NAP 4
mode_disp_end:
BRANCH mode,
[mode_zero,mode_one,mode_two,mode_three,mode_four,
mode_five,mode_six,mode_seven,mode_eight,mode_nine,
mode_A,mode_B,mode_C,mode_D,mode_E,mode_F]
'****************************************
'* MODE 0       *
'* for recording and checking
'* voice messages
'****************************************
mode_zero:
zero_loop:
if ALARM = 0 then P000_REC
if RST = 0 then P001_PLAY
INPUT LRED
INPUT LGREEN
PLAYL = 1
REC = 1
goto P002:
P000_REC:
HIGH LRED
LOW LGREEN
REC=0
goto P002
P001_PLAY:
LOW LRED
HIGH LGREEN
GOSUB say_message
P002:
goto zero_loop
'****************************************
'* MODE ONE
'* multi message recording
mode_one:
BTEMP=0
BTEMP2=0
state_start:
debug "state_start",cr
CNT=0
```

-continued

APPENDIX A

```
PLAYL = 1
REC = 1
A4 = 1
BUTTON P_RST,0,255,255,BTEMP,1,state_playback
BUTTON P_ALARM,0,255,255,BTEMP2,1,state_record_start
GOTO state_start
state_record_start:
debug "state_record_start",cr
REC = 0 ' start recording
state_record:
debug "state_record",cr
if ALARM = 0 then state_record ' loop while button held
goto state_post_record1
state_post_record1:
debug "state_post_record1",cr
REC = 1 'stop recording
GOTO state_post_record2
state_post_record2:
debug "state_post_record2",cr
BUTTON P_RST,0,255,255,BTEMP,1,state_start
BUTTON P_ALARM,0,255,255,BTEMP2,1,state_record_start
goto state_post_record2
state_playback:
debug "state_playback",cr
gosub say_message
goto state_post_playback
state_post_playback:
debug "state_post_playback",cr
BUTTON P_RST,0,255,255,BTEMP,1,state_playback
BUTTON P_ALARM,0,255,255,BTEMP2,1,state_record_start
GOTO state_post_playback
CL_start:
READ minX1,WTEMP.lowbyte
READ minXh,WTEMP.highbyte
READ maxX1,WTEMP2.lowbyte
READ maxXh,WTEMP2.highbyte
Xmid=(WTEMP+WTEMP2-2000)/2/XSCALE
' debug "Xmin:",dec WTEMP, "Ymin:",dec WTEMP2,cr
' debug dec ? (WTEMP+WTEMP2)/2
' debug dec ? (WTEMP+WTEMP2)/2/XSCALE
' debug "Xmid:",dec Xmid, "XSCALE:",dec XSCALE,cr
READ minY1,WTEMP.lowbyte
READ minYh,WTEMP.highbyte
READ maxY1,WTEMP2.lowbyte
READ maxYh,WTEMP2.highbyte
Ymid=(WTEMP+WTEMP2-2000)/2/YSCALE
READ minZ1,WTEMP.lowbyte
READ minZh,WTEMP.highbyte
READ maxZ1,WTEMP2.lowbyte
READ maxZh,WTEMP2.highbyte
Zmid=(WTEMP+WTEMP2-2000)/2/ZSCALE
DEBUG "Xmid:", dec Xmid,cr
DEBUG "Ymid:", dec Ymid,cr
DEBUG "Zmid:", dec Zmid,cr
shockwindow=0
CL_0: 'start of check loop
PULSIN PX,1,WTEMP ' do all three axes as close to each other
PULSIN PY,1,WTEMP2 ' as possible
PULSIN PZ,1,WTEMP3
' debug dec ? WTEMP
' debug dec ? Xmid
' debug dec ? XSCALE
' debug dec ? WTEMP/XSCALE
' debug dec ? ((WTEMP-1000)/XSCALE)-(Xmid)
' debug dec ? ABS((WTEMP/XSCALE)-(Xmid))
WTEMP=ABS(((WTEMP-1000)/XSCALE)-(Xmid))
WTEMP=WTEMP*WTEMP
' GOSUB green_on
' DEBUG "X^2:",dec WTEMP,cr
WTEMP2=ABS(((WTEMP2-1000)/YSCALE)-(Ymid))
WTEMP=WTEMP2*WTEMP2+WTEMP
WTEMP2=ABS(((WTEMP3-1000)/ZSCALE)-(Zmid))
WTEMP2=WTEMP2*WTEMP2+WTEMP
WTEMP=SQR(WTEMP)
WTEMP2=SQR(WTEMP2)
' debug "shock",dec shock_cnt,cr
' check tilt
```

-continued

APPENDIX A

```
if WTEMP > tiltlim then CL_tilt_cnt
tilt_cnt=0
CL_end_tilt:
' check shock
if WTEMP2 > shocklim then CL_shock_cnt
shock_cnt=0
CL_end_shock:
if shockwindow = 0 then CL_end_shock_window
shockwindow=shockwindow-1
CL_end_shock_window
' do LED indications
if shock_cnt<=shock_cnt_thresh then CL_LED_not_red
GOSUB red_on
goto CL_0
CL_LED_not_red:
if tilt_cnt=0 then CL_LED_off
GOSUB green_on
goto CL_0
CL_LED_off:
GOSUB led_off
goto CL_0
CL_tilt_cnt:
if tilt_cnt > 100 then CL_tilt_cnt_time
tilt_cnt=tilt_cnt+1
goto CL_end_tilt
CL_tilt_cnt_time:
' debug "tilt",cr
if shockwindow>0 then CL_alarm
tilt_cnt=0
goto CL_end_tilt
CL_shock_cnt:
if shock_cnt >
shock_cnt_thresh then CL_shock_cnt_time
shock_cnt=shock_cnt+1
goto CL_end_shock
CL_shock_cnt_time:
' debug "shock",dec shock_cnt,cr
shockwindow=300
goto CL_end_shock
CL_alarm:
' debug "alarm",cr
shockwindow=0
' say message one
GOSUB reset_message_pointer
GOSUB say_message
GOSUB red_on
NAP 4
GOSUB led_off
CNT=0
'wait for button push
GOSUB red_on
FOR WTEMP=0 TO 5000
if RST = 0 then CL_abort_alarm
NEXT
Repeat_alarm:
GOSUB led_off
GOSUB reset_message_pointer
GOSUB skip_message
GOSUB say_message
NAP 5
goto Repeat_alarm
GOSUB reset_message_pointer
GOSUB skip_message
GOSUB say_message
NAP 5
GOSUB reset_message_pointer
GOSUB skip_message
GOSUB say_message
NAP 5
GOSUB reset_message_pointer
GOSUB skip_message
GOSUB say_message
CL_abort_alarm
goto CL_0
CL_button_alarm
'alarm caused by pressing the red button
GOSUB reset_message_pointer
```

-continued

APPENDIX A

```
GOSUB skip_message
GOSUB skip_message
GOSUB say_message
goto CL_0
CL_end:
goto CL_0
mode_two:
tiltlim=50
shocklim=80
shock_cnt_thresh=0
goto CL_start
mode_three:
tiltlim=50
shocklim=80
shock_cnt_thresh=1
goto CL_start
mode_four:
tiltlim=50
shocklim=80
shock_cnt_thresh=2
goto CL_start
mode_five:
tiltlim=50
shocklim=80
shock_cnt_thresh=3
goto CL_start
mode_six:
tiltlim=50
shocklim=80
shock_cnt_thresh=4
goto CL_start
mode_seven:
tiltlim=50
shocklim=90
shock_cnt_thresh=0
goto CL_start
mode_eight:
tiltlim=50
shocklim=90
shock_cnt_thresh=1
goto CL_start
mode_nine:
tiltlim=50
shocklim=90
shock_cnt_thresh=2
goto CL_start
mode_A:
tiltlim=50
shocklim=90
shock_cnt_thresh=3
goto CL_start
mode_B:
tiltlim=50
shocklim=100
shock_cnt_thresh=0
goto CL_start
mode_C:
tiltlim=50
shocklim=100
shock_cnt_thresh=1
goto CL_start
mode_D:
mode_E:
mode_F:
mode_not_zero:
loop:
goto loop
say_message:
PLAYL=0
NAP 2
PLAY LOOP: ' wait for end of message
if RECLED=1 and ALARM = 1 then PLAY_LOOP
PLAYL=1
RETURN
reset_message_pointer:
A4 = 0 ' reset address counter in message chip
nap 0
```

-continued

APPENDIX A

```
A4 = 1
RETURN
skip_message:
A0 = 1 ' skip through message
PLAYL=0
NAP 0
PLAYL=1
A0 = 0 ' do not skip next message
NAP 0
RETURN
red_on:
LOW LGREEN
HIGH LRED
RETURN
green_on:
HIGH LGREEN
LOW LRED
RETURN
led_off:
INPUT LRED
INPUT LGREEN
RETURN
wait_for_ALARM_button:
BTEMP=0
WFAB1:
' wait for red button to be pushed
BUTTON 10,0,255,255,BTEMP,1,WFAB2
goto WFAB1:
WFAB2:
RETURN
'settle_loop:
'SLL2:
' CNT=0
' WTEMP=SETTLE_VAL
'SLL3:
' PULSIN SETTLE_PIN,1,SETTLE_VAL ' read pulse width
' debug "S:",DEC SETTLE_VAL,cr
' if ABS(WTEMP-SETTLE_VAL) >
SETTLE_THRESHOLD then SLL2
' CNT=CNT+1 ' has to stay within
SETTLE_THRESHOLD for SETTLE_TIME samples
' if CNT<SETTLE_TIME then SLL3
'RETURN
```

We claim:

1. An emergency signal device comprising:

a pre-programmed microprocessor, said microprocessor capable of accepting serial and parallel data input and having primary check and alarm modes and having pre-programmed attitude and shock algorithms and thresholds and having pre-programmed attitude and delay timing routines;

means for detecting the attitude of said emergency signal device, said means for detecting the attitude having data output capable of being received by said microprocessor;

means for recording and storing multiple voice and alarm signals capable of activation by a signal from said microprocessor and having input means to record multiple voice messages; and an external speaker for playing said multiple voice messages and alarm signals.

2. The emergency signal device of claim 1 further comprising means of manually activating and de-activating said alarm mode.

3. The emergency signal device of claim 1 further comprising a periodic messaging mode.

4. The emergency signal device of claim 1 father comprising means to detect the exit of said emergency signal device from an acceptable geographic area.

5. The emergency signal device of claim 1 further comprising a means to activate existing telephone emergency notification systems.

6. An emergency signal device comprising:

a pre-programmed microprocessor, said microprocessor capable of accepting serial and parallel data input and having primary check and alarm modes and having pre-programmed attitude and shock algorithms and thresholds and having preprogrammed attitude and delay timing routines;

means for detecting the attitude of said emergency signal device, said means for detecting the attitude having data output capable of being received by said microprocessor;

means for storing multiple pre-recorded voice and alarm signals capable of differential activation by a signal from said microprocessor; and an external speaker for playing said multiple voice messages and alarm signals.

* * * * *